(12) United States Patent
Armbruster et al.

(10) Patent No.: US 7,964,363 B2
(45) Date of Patent: Jun. 21, 2011

(54) DIRECT DETERMINATION OF VITAMIN D IN SERUM OR PLASMA

(75) Inventors: Franz Paul Armbruster, Bensheim (DE); Heinz-Juergen Roth, Heidelberg (DE); Sabine Friedl, Bensheim (DE); Claudia Schumann, Weinheim (DE)

(73) Assignee: Immundiagnostik AG, Benshein (DE)

( * ) Notice: Subject to any disclaimer, the term of this patent is extended or adjusted under 35 U.S.C. 154(b) by 233 days.

(21) Appl. No.: 12/517,754

(22) PCT Filed: Jan. 30, 2008

(86) PCT No.: PCT/EP2008/051162
§ 371 (c)(1),
(2), (4) Date: Jun. 4, 2009

(87) PCT Pub. No.: WO2008/092917
PCT Pub. Date: Aug. 7, 2008

(65) Prior Publication Data
US 2010/0068725 A1    Mar. 18, 2010

(30) Foreign Application Priority Data

Feb. 1, 2007  (DE) .......................... 10 2007 005 099

(51) Int. Cl.
*G01N 33/53* (2006.01)
(52) U.S. Cl. .......................... 435/7.1; 435/7.2; 436/518
(58) Field of Classification Search .................. None
See application file for complete search history.

(56) References Cited

FOREIGN PATENT DOCUMENTS
| WO | WO 02/46746 A2 | 6/2002 |
| WO | WO 03/023391 A2 | 3/2003 |
| WO | WO 2004/063704 A2 | 7/2004 |

*Primary Examiner* — Jacob Cheu
(74) *Attorney, Agent, or Firm* — Dickstein Shapiro LLP

(57) ABSTRACT

A method for quantitating vitamin D metabolites directly in blood plasma or serum, without the need for prior purification of the vitamin D metabolites, comprising a digestion of the serum proteins with a serine protease such as proteinase K and sequence of steps for inhibiting the proteinase K activity in the competitive binding analysis. The advantages of this method are its high accuracy over the whole range of physiologically relevant values and that it can be easily adapted for a fully automated analysis of serum and plasma samples.

11 Claims, 4 Drawing Sheets

DIRECT DETERMINATION OF VITAMIN D IN SERUM OR PLASMA

FIELD OF THE INVENTION

The invention concerns a method for quantitative determination of vitamin D in serum or plasma.

BACKGROUND OF THE INVENTION

Human can form vitamin $D_3$ (cholecalciferol) in the skin with the help of sunlight. Vitamin $D_2$ (ergocalciferol) is taken up with food. Even though vitamin $D_2$ and $D_3$ slightly differ in their side chains they have identical biological activity. They are both bound in circulation by the vitamin D binding protein (VDBP) and metabolised in liver to 25-hydroxyvitamin D. 25-hydroxyvitamin D is the storage form in the body and the vitamin D metabolite with the highest concentration in serum or plasma. When needed, it is hydroxylated in the kidney to 1α,25-dihydroxyvitamin D (the so-called D-hormone) which is the biologically active form and regulating the absorption of calcium in the intestines, the mineralisation of the bones, the differentiation of osteoplasts, the synthesis of bone matrix and, among others, also the neuromuscular functions. Even a tiny deficiency of less than 15 ng 25-hydroxyvitamin D per mL serum (37.5 nmol/L 25-OH-Vit.D/L) causes a rise of the parathormon level and increased bone resorption, due to the reduced calcium absorption (Chapuy M C et al. in J Clin Endocrinol Metab 1996; 81:1129-33). Vitamin D deficiency is an important risk factor for senile osteoporosis. An early diagnosis and vitamin $D_2$ supplementation allow an effective prevention of bone fractures. A heavy vitamin D deficiency of less than 5 ng 25-hydroxyvitamin D per mL serum (12.5 nmol/L) causes rickets in children and osteomalacia in adults (Scharla et al. Exp Clin Endocrinol. Diabetes, 1996, 104:289-292). Excess of vitamin D due to overdosing causes hypercalcaemia. During winter about one third of the population in Germany above 50 years of age suffer from vitamin D deficiency due to the darkness (Scharla et al., Osteoporose Int. 1998; 8 (Supplement 2):S7-S12). Younger people can also suffer from vitamin D deficiency, due to gastro-intestinal diseases, liver dysfunction, maladsorption, or drug-induced heightened metabolism, for example caused by antiepileptica.

Conventional lab techniques for the determination of 25-hydroxyvitamin D in serum and plasma are very laborious (Tanner et al. (1988), *J. Assoc. of Analyt. Chem.*, 17, 607-710). Furthermore, U.S. Pat. No. 5,981,779 (Holick et al), WO 89/01631 and EP 0 583 945 (DeLuca et al) teach vitamin D testing based on the binding to VDBP. To achieve that, the vitamin D metabolites first have to be extracted from the plasma or serum using organic solvents, and then purified by chromatography. WO 99/67211 (Armbruster et al) teaches a sample preparation involving the precipitation of the plasma and serum proteins by ethanol. The protein precipitate is then removed by centrifugation and the ethanol supernatant, comprising the soluble vitamin D metabolites, is used in the binding assay. EP 0 753 743 (Hollis) teaches the preparation of the plasma or serum sample using periodate precipitation. The quantification of the vitamin D compounds is then carried out in the protein-free supernatant. DE 10144 905 (Armbruster et al) describes a method for determining vitamin D directly in plasma or serum wherein a soluble salicylic compound is added to the serum or plasma to release the 25-hydroxyvitamin D from the VDBP. The amount of 25-hydroxyvitamin D in the plasma or serum is then determined directly using antibodies.

The sample preparation methods mentioned above are either laborious or prone to errors or both. It is the object of the present invention to provide a simple and reliable method for the direct quantitative determination of 25-hydroxyvitamin D in serum or plasma.

SHORT DESCRIPTION OF THE INVENTION

This problem is solved by the method according to claim 1. Preferred embodiments of the method are disclosed in dependent claims.

According to the present invention, the direct method for the quantitative determination of vitamin D metabolites in blood plasma or serum by competitive binding analysis, without the need for purification of the vitamin D metabolites from the blood plasma or serum includes the following steps: (a) addition of an appropriate amount of a serine protease with endo- and exoproteolytic activity such as proteinase K to a sample containing blood plasma or serum and digestion of the vitamin D binding proteins in the blood plasma or serum, until they can no longer bind any more vitamin D metabolites; (b) dilution of the sample containing the serine protease, the vitamin D metabolites and the digested plasma or serum proteins using a dilution buffer, in which the serine protease is substantially inactive; (c) provision of a vitamin D tracer composition, which is coupled to a solid phase; (d) provision of an antibody, preferably a monoclonal antibody against the relevant vitamin D metabolites, wherein said antibody is substantially resistant to the endoproteolytic activity of the used serine protease, and (e) combination of the sample with the vitamin D metabolites (analyte), the solid phase with the vitamin D tracer compound and the monoclonal antibody for a predetermined period, and conducting during a set period of time a competition binding reaction of the vitamin D metabolite and the vitamin D tracer on the monoclonal antibody in a binding buffer, in which the serine protease is essentially inactive and no unspecific binding between vitamin D and remaining serum proteins can occur, and (f) separation of the solid phase with the vitamin D tracer compound and optionally bound monoclonal antibody from the binding buffer, and optionally washing of the solid phase; and (g) determination of the amount of monoclonal antibody on the solid phase, and (h) determination of the amount of vitamin D metabolite in the blood plasma or serum using comparative data.

In one preferred embodiment of the method, the binding analysis is carried out at a pH-value between 3.0 and 10.0 in the presence of 0.1 to 5.0% (w/v) gelatin, 1 to 10 mmol/L EDTA or EGTA, and optionally serine protease inhibitors, and 0.005 to 0.050% (w/v) β-mercaptoethanol. The antibody used in steps (d) and (f) may also be a mixture of monoclonal antibodies, which specifically bind 25-hydroxyvitamin $D_3$ and 25-hydroxyvitamin $D_2$ respectively. In one embodiment of the invention, the monoclonal antibody can bind 25-hydroxyvitamin $D_3$ or 25-hydroxyvitamin $D_2$ or both. In a different embodiment of the method of the invention, the monoclonal antibody can bind 1α,25-dihydroxyvitamin $D_2$ or 1α,25-dihydroxyvitamin $D_3$ or both dihydroxyvitamin D metabolites.

The vitamin D metabolite determined by the method according to the invention is chosen from 25-hydroxyvitamin $D_2$, 25-hydroxyvitamin $D_3$, 1α,25-dihydroxyvitamin $D_2$, 1α,25-dihydroxyvitamin $D_3$. The protein binding analysis and subsequent quantitative determination are preferably carried out in an ELISA (enzyme-linked immunosorbent assay), RIA (radio-immunoassay), FIA (fluorescence immunoassay), LIA (luminescence immunoassay), ILMA (immunoluminometric assay) or ECLA (electrochemical luminescence assay). The amount of bound monoclonal antibody is preferably determined using a second antibody. The second antibody then normally is one of a different species. The monoclonal antibody for the binding analysis may also be coupled to a quantifiable colour, enzyme, fluorescence, luminescence, chemoluminescence (e.g. acridine) or electroluminescence (e.g. ruthenium complex) marker.

A further aspect of the invention concerns a test kit for carrying out the above mentioned method, including one or more antibodies specific for vitamin D metabolites, a vitamin D tracer coupled to a solid phase, proteinase K, and appropriate buffer solutions. Preferred buffer solutions in the test kit of the invention comprise a digestion buffer with agents denaturing and unfolding vitamin D binding proteins which are then digested and destroyed by a serin protease such as proteinase K, an assay buffer, preferably comprising proteinase K inhibiting substance and a salicylic releasing agent, preferably salicylic acid in amount from 0.1 to 1.0 Mol/L, to avoid unspecific back-binding of vitamin D to partly digested serum proteins.

As mentioned above, in the method of the invention, the plasma or serum sample is treated prior to analysis with proteinase K in such a way that all plasma or serum proteins which may bind vitamin D metabolites are digested and broken down such that they can no longer bind 25-hydroxyvitamin D or any other vitamin D metabolites in any way. This is achieved preferably by digestion with proteinase K, most preferably in the presence of protein denaturing agents and vitamin D releasing agents so that the protein D binding proteins unfold and become digested by the protease. Afterwards, an aliquot of the proteinase K treated serum or plasma is diluted in a buffer solution which inhibits and stops the activity of proteinase K and which prevents unspecific or specific binding of vitamin D metabolites to the remaining serum proteins, and the amount of the wanted vitamin D metabolite in the sample is quickly determined using competition binding analysis on antibodies, preferably monoclonal antibodies which are substantially resistant to proteinase K. As mentioned above, a complete digestion of the vitamin D binding proteins can be ensured by the addition of denaturing agents prior to digestion with a serine protease. Useful protein denaturing agents are SDS (0.1%), detergents, and vitamin D releasing agents such as acidic denaturing agents such as salicylic acid, warfarin, sulfonic acids, toluene sulfonic acids, naphthalene sulfonic acid, anilinonaphthalene sulfonic acids (ANS), notably 1-anilinonaphthalene-8-sulfonic acid (1,8-ANS) and 8-anilinonapthalene-1-sulfonic acid (8-ANS), salicylic acids and derivatives thereof, preferably in an effective concentration of 0.01 to 20 mg/mL, more preferably 0.1 to 10 mg/mL, most preferably in amounts of no less than 0.5 mg/mL serum. The amounts and type of denaturing agent must be chosen and selected individually for each serum protease Compared to earlier methods, the method according to the invention has the advantage that the vitamin D binding proteins cannot interfere with the measurements after their digestion. It should be noted that, apart from VDBP, many other proteins can bind vitamin D, e.g. albumin, fetoprotein etc., and that these proteins are abundant in serum. Even though these proteins are largely separated from the vitamin D metabolites in the conventional precipitation using ethanol or periodate according to known methods, some remaining quantities may stay in the sample and may renatured during the competition binding analysis when the buffer is changed, and which can then interfere with the binding analysis. The remaining protein quantities can also bind to the wall of the vessel, or to the solid phase, and, depending on which type is used, even to the vitamin D tracer, which grossly falsifies the measurement. The use of vitamin D displacement agents such as salicylic compounds or warfarin in releasing and binding buffers does not solve this fundamental problem.

The problem is fundamentally shifted by the treatment of the blood serum or plasma with proteinase K. Firstly, such enzymatic treatment of the plasma and serum protein is an established procedure, which is easy to control, and there is no risk of unexpected precipitation. Secondly, as opposed to a denaturing precipitation, proteins cannot renature after digestion, not even after a change of medium or buffer. Third, the digestion can be extended at will, until the measuring results are stabilised, or intensified and complemented by the addition of denaturing agents and vitamin D releasing agents. Fourth, digestion using proteinase K can easily be automatised as opposed to protein precipitation. Therefore the only remaining problem is to ensure that the competition binding analysis is not disturbed by the presence of proteinase K. According to the invention, this problem is solved by a change in pH conditions, the dilution of proteinase K in a gelatin-containing buffer and, more generally, by changing the conditions so they inhibit the activity of proteinase K. The activity of proteinase K can further be inhibited by the addition of EGTA.

EGTA is the chemical compound ethylene glycol tetraacetic acid, a chelating agent that is related to the better known EDTA, but with a much higher affinity for calcium than for magnesium ions. It is useful for making buffer solutions that resemble the environment inside living cells, where calcium ions are usually at least a thousandfold less concentrated than magnesium. The pKa for binding of calcium ions by tetrabasic EGTA is 11.00 and EGTA is further an inhibitor of proteinase K. Further, the competition binding analysis according to the present invention is characterised by the use of binding partners which are substantially resistant to proteinase K. The competition binding analysis according to the invention involves further multiple washes which quickly dilute and wash out non-binding proteins such as proteinase K from the assay system. Remaining quantities of proteinase K on the wall of the vessel or in the solid phase are to be avoided, and if, they do not interfere with the binding analysis or the determination of the amount of bound antibodies.

Further advantages, features and embodiments of the invention are disclosed in the detailed description of the invention, the examples and the drawings.

DETAILED DESCRIPTION OF THE INVENTION

Figure 1:
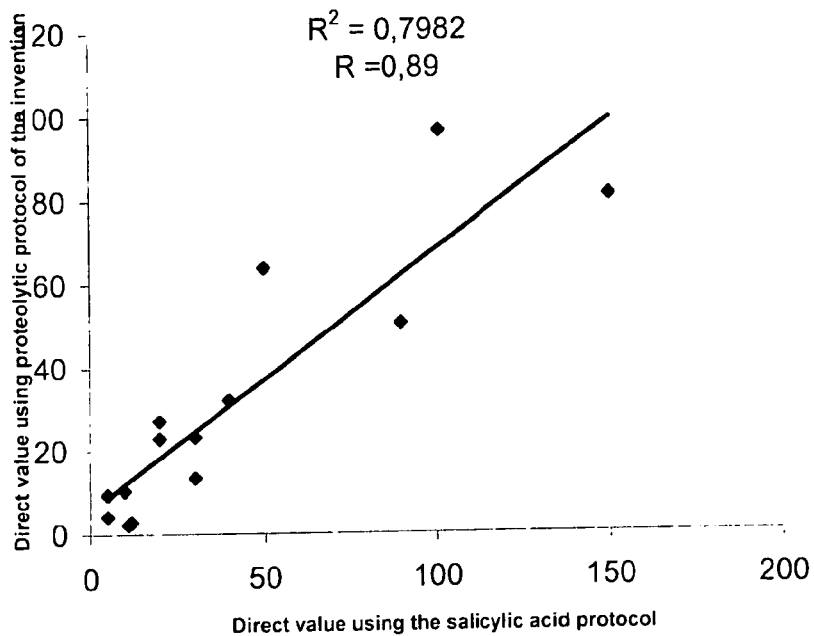
FIG. 1 shows a graphical representation of the correlation between directly measured serum 25-hydroxyvitamin D values as determined by an ELISA (1 h proteinase K digestion at 37° C.) in accordance with Example 1 of the invention, and values determined by an ELISA making use of a conventional salicylic acid dissociation reagent.

Proteinase K is a highly active subtilisin-type serine protease form the fungus *Tritirachium album* of mass 28.904 Da (Roelcke, D. and Uhlenbruck, G. (1969) Z. Med. Mikrobiol. Immunol. 155, 156-170). The enzyme has a broad specificity for native and denatured proteins and is commonly used in the purification of DNA and RNA. Denaturation agents such as sodium dodecyl sulphate (SDS) or urea, as well as raised temperatures of 50 to 60° C. enhance its activity. The recommended concentration is 50 to 100 μg/mL for protein removal and enzyme activation, and up to 2 mg/mL for tissue treatment. In the removal of plasma and serum proteins, proteinase K was preferably used in a final concentration of 100 to 300 μg/mL serum at 37 to 50° C. Proteinase K is normally prepared in a stock solution of 20 mg/mL (600 mAU/mL) from a lyophilised powder, and stored at −20° C. until use. The enzyme is active at a range of pH 7.5 to 12. It reaches its maximal catalytic activity at 50 to 60° C. Proteinase K requires the presence of calcium ions for stability, but not for proteolytic activity. According to the invention, the digestion of the proteins in the blood plasma or serum normally occurs over a period of 60 minutes at 25 to 50° C., preferably at 30 to 40° C., most preferably 37° C. with 200 μg/mL proteinase K (from a stock solution containing 20 mg proteinase K/mL in 50 mM Tris HCl, pH 8.0; 10 mM $CaCl_2$), optionally in the presence of in the presence of 0.1% SDS or a vitamin D releasing agents such as warfarin, 8-ANS, 1,8-ANS, toluene sulfonic acids and the like, most preferably in the presence of 0.1 to 10 mg/mL, most preferably 0.5 to 2 mg/mL 8-ANS.

X-ray diffraction crystallographic studies have shown that proteinase K has two calcium binding sites (Bajorath et al., 1989, Nature 337, 481-484). Even though $Ca^{2+}$ is not directly participating in the catalytic mechanism, its removal reduces the activity of proteinase K to about 20% of the original value; measured using a synthetic Succinyl-Ala-Ala-Ala-p-nitroanilid substrate standard. According to the invention, the removal of $Ca^{2+}$ is achieved by the addition of sequestering and chelating agents, such as ethylene diamine tetraacetate (EDTA) or ethylene glycol tetraacetate (EGTA) in a concentration of for example 2 to 10 mmol/mL. Proteinase K is further deactivated by serine protease inhibitors such as phenylmethylsulfonylfluoride (PMSF), diisopropylfluorphosphate (DFP) or 4-(2-Aminoethyl) benzenesulfonyl fluoride (AEBSF). AEBSF has a similar spectrum of activity than PMSF, but is considerably more stable, especially in a low pH environment. Typically, solutions with a concentration of 0.1 to 1 mM are used. Sulfhydryl reagents, such as para-chloromercurybenzoate (PCMB), L-1-tosylamido-2-phenylethychloromethylketone (TPCK), N-alpha-p-tosyl-L-lysyl-chloromethylketone, N-ethylmaleimide (NEM), iodacetamide, and o-phenanthroline, have only limited influence on the activity of proteinase K.

The pH of the sample is set to 3.0 to 10.0, preferably 7.0 to 8.0 for the protein binding analysis on the antibody. In an especially preferred embodiment, the protein binding analysis on the antibody is carried out at a pH of 6.0 to 8.0. Further, the buffers contain an excess of the sequestering and chelating agents such as ethylene diamine tetraacetate (EDTA) or ethylene glycol tetraacetate (EGTA), for example between 2 and 10 mmol/mL, in order to bind free $Ca^{2+}$. It is not necessary to add $Ca^{2+}$ ions for the proteinase K digestion, since the natural calcium concentration in the serum is sufficient, to offset any remaining activity of the protease Finally, the dilution buffer for the protein binding analysis contains 0.5 to 10% by weight of gelatin, preferably 0.5 to 2% by weight of gelatin, as well as 1 mmol/L β-mercaptoethanol. Hence, the binding buffer preferably contains a buffer with 50 mmol/L $NaH_2PO_4/Na_2HPO_4$ buffer, pH 6.0 to 10.0 (preferred pH 8.0), 1 to 2% gelatin (preferred 0.05 to 0.5%), 2-5 mmol/L EGTA, 0.005-2 mM β-mercaptoethanol (preferred 0.005% by weight), as well as optionally a proteinase K inhibitor.

Optionally, 0.1 to 5% by weight, preferably 1 to 3% by weight, natural and/or chemically modified cyclodextrin can be added, in order to prevent interference of free fatty acids, cholesterol and other lipids in the binding analysis. In one preferred embodiment, the washing and dilution buffers therefore contain cyclodextrin, for the sequestering and masking of interfering molecules such as fatty acids, cholesterol etc. The cyclodextrin is preferably added by 0.1 to 10% by weight, preferably 0.2 to 7.5% by weight, most preferably in 1 to 5% by weight, based on the final concentration in the sample. The cyclodextrin can also be chemically modified, for example with methyl, ethyl, propyl, hydroxyethyl, 2-hydroxypropyl, glycosyl, maltosyl, carboxymethyl groups. Natural cyclodextrins and 2-hydroxypropyl-β-cyclodextrin are especially preferred.

The method according to the invention is suitable for the quantitative determination of 25-hydroxyvitamin $D_2$, 25-hydroxyvitamin $D_3$, and, in an alternative embodiment, for the determination of 1α,25-dihydroxyvitamin $D_2$ and 1α,25-dihydroxyvitamin $D_3$. Purification of the sample is required if the concentration of D-hormone is to be determined, apart from the vitamin D storage form. The D-hormone is identified by binding to an antibody, which is specific for the dihydroxy-species. Monoclonal antibodies, which are specific for the D-hormone, but not 25-hydroxyvitamin D, are known.

The protein-binding assay according to the invention can be carried out as an ELISA (enzyme linked immunosorbent assay) or a RIA (radioimmunoassay). Especially preferred are non-radioactive systems based on fluorescent and chemoluminescent markers (FIA or LIA). If the vitamin D tracer is coupled to an enzyme, for example to an alkaline phosphatase or a fluorescent or chemoluminescent marker, then the solid phase or the wall of the reaction vessel is normally coated with antibodies against the vitamin D compound which is to be determined.

In the method according to the invention, it is advantageous that the quantitative determination of the vitamin D metabolites can be carried out directly in a liquid sample such as serum of plasma. The sample does not need preparation such as the problematic protein precipitation, organic extraction and/or column chromatography. Instead, the vitamin D metabolites that are to be determined are disassociated from their binding sites by protease K digestion of the vitamin D binding proteins (VDBP, albumin and many others). Of course, salicylic compounds can disassociate vitamin D metabolites from a protein in vitro, but this procedure cannot avoid the participation in the binding analysis of diverted proteins in reactivated form. Our analyses suggest that the vitamin D binding protein/salicylate complex is also absorbed on the wall and will later also bind vitamin D tracer. As mentioned earlier, the vitamin D binding proteins do not only comprise the highly specific VDBP (Gc-globulin or group-specific component), but also abundant proteins such as albumin, α-fetoprotein and many others. These proteins can also bind 25-hydroxyvitamin D and 1α,25-dihydroxyvitamin D with more or less high specificity and affinity. If the purification of the vitamin D samples is comparatively incomplete, such as in the case of protein precipitation by ethanol or by denaturation, then proteins which remind in the sample solution may bind to the vitamin D tracer during the competition binding assay, and the quantitative vitamin D determination is dependant on coincidences, such as the completeness of the protein precipitation or the amount of cholesterol in the sample. Organic extraction and/or chromatographic purification of the vitamin D compounds do not improve the quantitative determination, because these steps also influence and change the amount of traceable vitamin D, depending on the properties of the sample—among others on how many vitamin D binding proteins are present in the sample, and on whether it is lipaemic etc. On the other hand, the method according to the present invention has the advantage that an error prone purification of the vitamin D metabolites is not necessary and the protein-binding assay is directly carried out in the plasma or serum.

The invention also comprises the use of vitamin D derivatives of formula I:

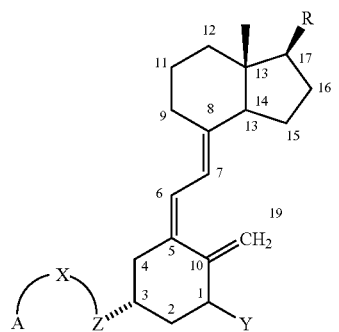

(I)

wherein Z is the oxygen or sulphur atom of an ether group or a carbon; X is a substituted or unsubstituted hydrocarbon moiety of 0.8 to 4.2 nm length; Y is hydrogen or hydroxyl group; A is a solid phase (vessel wall, beads, labelled solid particles or magnetic particles), or a functional group, which may be bound by a proteinase K-durable protein with high affinity, for example monoclonal antibodies or streptavidin, for the coupling of the functional vitamin D-derivative to the solid phase; R is the side-chain of the vitamin D metabolite, preferably the 25-hydroxylated side-chain of vitamin $D_2$ or vitamin $D_3$.

The linker X is a $C_8$- to $C_{12}$-group, which may contain common heteroatoms such as S, O, N or P, a peptide, a ketone or a substituted or unsubstituted amino-polyether moiety with a length of 0.8 to 4.2 nm, preferably about 0.9 to 1.5 nm, most preferably an amino-undecanoic acid or a hexamido, octamido or decamido-amidopropyl linker group. This gap between group A and the vitamin D antigen determinant, comprising side-chain R and group Y, allows that the monoclonal antibodies can bind without interference from the solid phase. Preferred are 25-hydroxyvitamin D-3β-3-[6-N-(biotinyl)hexamido]amidopropylether and the corresponding 1α,25-dihydroxyvitamin D Biotin compound, which are coupled to the solid phase via streptavidin.

The method according to the invention therefore allows for a non-radioactive quantitative determination of 25-hydroxyvitamin D and 1α,25-dihydroxyvitamin D in serum or plasma without the need for complex sample preparation. Hence, the method is especially suitable for sequential testing for osteoporosis prophylaxis.

A further aspect of the invention concerns a reagent kit for the determination of vitamin D metabolites such as 25-hydroxyvitamin D and 1α,25-dihydroxyvitamin D, which comprises among others a functional vitamin D derivative and an appropriate proteinase K solution. Optionally, the kit comprises anti-vitamin D antibodies, which means antibodies against 25-hydroxyvitamin $D_{2/3}$ or 1α,25-dihydroxyvitamin $D_{2/3}$ or different vitamin D metabolites, coated microtiter plates and/or magnetic or other microparticles and reagents.

In principle, instead of plasma or serum samples, foodstuffs, such as milk or cheese etc. can be analysed directly for their vitamin D content. In certain cases, it can be obvious to remove interfering substances by extraction or precipitation from the sample, depending on the character of the matrix. The interference of the vitamin D binding proteins which remain after purification can then be removed by digestion with proteinase K.

EXAMPLE 1

Determination of 25-hydroxyvitamin D in Serum or Plasma (i) Binding of the Vitamin D Tracers to a Solid Phase 25-hydroxyvitamin D-3β-3-[6-N-(biotinyl)hexamido]amidopropylether was coupled to a solid phase via streptavidin. For this, portions of 100 ng streptavidin were first introduced into the cavities of a microtiter plate, dissolved in 200 μL 60 mM sodium bicarbonate at pH 9.6, and the plate was incubated overnight at 4° C. The streptavidin solutions were then removed and the cavities were washed 5 times with 200 μL washing buffer solution (50 mmol/L phosphate buffer, pH 6.0, 0.05% Tween-20). Next, 250 μL block buffer (phosphate buffer, pH 6.0 with 0.5% casein, 1% gelatin, 1% thimerosal) was filled into each cavity, incubated for 1 hour and then removed, and then each cavity was washed again 5 times with 200 μL washing buffer. Then, 10 ng 25-biotin-hydroxyvitamin D in 200 μL washing buffer was introduced into each of the cavities, incubated over night in the dark under shaking at 2 to 8° C., the biotin-vitamin D solutions removed and the cavities again washed 5 times with 200 μL washing buffer. This was followed by the binding of a monoclonal mouse antibody (ID2) with vitamin D in the presence of 25-hydroxyvitamin D from the liquid standard or a sample.

(ii) Sample Handling and Preparation

The serum and plasma samples were only stored for a short period of time at room temperature. If the analysis was carried out within 24 hours from the sample collection, the sample was stored at 4 to 8° C. Otherwise, the samples were stored at −20° C. until analysis. Multiple freezing and defrosting of the sample was avoided. Hemolysis does not interfere with the results. Whole blood may not be used as sample material. Lipaemic samples were centrifuged for 10 minutes at approximately 30,000×G, and the aqueous phase was then removed through the supernatant fatty layer using a pipette. In the case of strongly lipaemic samples, a delipidation kit was used.

80 µl blood plasma or serum was added to 800 µL proteinase K solution (200 µg/mL proteinase KL in 50 mM Tris.HCl, pH 8.0; 10 mM $CaCl_2$, 10% SDS or 1 mg/mL 8-ANS), well mixed and incubated for 1 hour at 37° C. in a water bath. During this the proteinase K breaks down VDBP (Gc-Globulin) and other vitamin D binding serum proteins such as albumin to such an extent that they cannot bind 25-hydroxyvitamin $D_{2/3}$ or dihydroxyvitamin $D_{2/3}$ any longer.

(iii) Competitive Binding

200 µL monoclonal mouse anti-25-OH-vitamin D antibody (1:125,000) in washing buffer (50 mM phosphate buffer, pH 8.0, 2.0 mM EGTA, 0.005% β-mercaptoethanol, 0.1% (w/v) gelatin, optionally, 0.5 to 10% salicylic acid) and 20 µL standard, control or sample were introduced into each of the cavities. The microtiter plate was shaken for over night in the dark at 8 to 10° C. The 25-hydroxyvitamin D in the sample would then compete with the vitamin D tracer on the wall for the binding sites on the monoclonal anti-vitamin D antibody. The solutions were then removed from the cavities and the cavities were each washed 5 times with 250 µL washing buffer.

The pH, the gelatin in the buffer and the removal of free $Ca^{2+}$ by EGTA brought about that the monoclonal antibody was not broken up by any the remaining quantity of proteinase K during the competition binding analysis. However, the vitamin D binding proteins present in the sample, such as serumalbumin, could not longer bind to the vitamin D tracer, which often leads to erroneously high vitamin D contents in the state of the art.

(iv) Determination of Competitive Binding

200 µL conjugate (marked with goat-anti-mouse-MAB antibody peroxidase) was dissolved 1:2,500 in washing buffer, introduced into the cavities, and incubated for an hour at room temperature while shaking. The solutions were then removed and the cavities each washed 5 times with 250 µL washing buffer. For the colour reaction, 200 µL tetramethylbenzidine(TMB)-substrate solution (of BioFX Laboratories Inc.) was introduced into the cavities. After 20 minutes, the colour generation was stopped by addition of 50 µL 2 M $H_2SO_4$ per cavity. The optical density measurements were carried out in a photometer at 450 nm with 620 nm reference wavelength (or 690 nm).

EXAMPLE 2

Analytical Sensitivity of the Proteolytic Testing System According to the Invention For the determination of the detection limit of the testing system according to the invention, the competition binding and measurement was essentially carried out as in Example 1, except that the sample contained no or defined standard amounts of vitamin D metabolite. The results are shown in the table I below.

TABLE I

Detection limit of 25-hydroxyvitamin D in a proteolytic system

| Sample with 0 nmol Vit.D/L | | Optical Density of the standard Calibration curve | | |
|---|---|---|---|---|
| 40x | | OD 1 | OD2 | Standard nmol/L |
| 1.388 | 1.424 | 1.442 | 1.374 | 0 |
| 1.438 | 1.376 | 1.172 | 1.196 | 6.4 |
| 1.46 | 1.376 | 0.988 | 0.871 | 16 |
| 1.369 | 1.409 | 0.63 | 0.554 | 40 |
| 1.504 | 1.463 | 0.373 | 0.312 | 100 |
| 1.418 | 1.339 | 0.269 | 0.25 | 250 |
| 1.396 | 1.34 | | | |
| 1.476 | 1.401 | | | |
| 1.37 | 1.318 | | | |
| 1.424 | 1.449 | | | |
| 1.554 | 1.36 | | | |
| 1.354 | 1.373 | | | |
| 1.404 | 1.392 | | | |
| 1.386 | 1.413 | | | |
| 1.421 | 1.398 | | | |
| 1.48 | 1.439 | | | |
| 1.382 | 1.43 | | | |
| 1.366 | 1.411 | | | |
| 1.328 | 1.469 | | | |
| 1.415 | 1.476 | | | |

The mean OD for the blank sample was 1.41, with a standard deviation of 0.05 OD. The detection limit of 25-hydroxyvitamin D was only 2 nmol/L, which is about 0.8 ng/L (mean value−2× standard deviation, inserted in the calibration curves), which is fully sufficient for the determination of physiologically relevant range of vitamin D concentrations in serum).

EXAMPLE 3

Reproducibility of the Proteolytic System

The correspondence between the independent measurements for the proteolytic system 1 was determined. The precision results from the standard deviation and the relative standard deviations (the variation coefficients) between the discrete values and the mean. A standard serum sample was used as a positive reference sample. The mean concentration was 41.4 nmol 25-OH-Vit.D/L. For the remaining values, the determined detection limit were used. The results for the serum sample are shown in Table II.

TABLE II

Intra-assay variance of the proteolytic method

| | Calibration curves | | |
|---|---|---|---|
| 1 Sample, 20 runs: | OD1 | OD2 | Standard nmol/L |
| | 1.442 | 1.374 | 0 |
| Mean Optical Density: 0.622 | 1.196 | 1.172 | 6.4 |
| | 0.988 | 0.871 | 16 |
| Mean Concentration: 41.4 nmol/L | 0.63 | 0.554 | 40 |
| | 0.373 | 0.312 | 100 |
| Intra-assay variance: 10% | 0.269 | 0.25 | 250 |

The precision between separate analysis series (inter-assays) represents the variations of one or more known and unknown factors. To achieve this, the above sample was prepared and analysed 10 times on different days. The results are shown in Table III.

TABLE III

Inter-assay variance of the proteolytic method

| INTER-ASSAY OF ONE SAMPLE 10 TIMES ON DIFFERENT DAYS | MEASUREMENT in nmol/L |
|---|---|
|  | 40.0 |
|  | 33.6 |
|  | 38.6 |
|  | 36.5 |
|  | 43.6 |
| Mean: 38.7 nmol/L | 38.1 |
|  | 44.8 |
|  | 38.0 |
| Stability value/Mean * 100 = CV | 38.0 |
|  | 35.8 |
| CV in % | 8.31 |

Hence, the inter-assay variance is 8.31%.

EXAMPLE 4

Method Comparison and Correlation Analysis

The accuracy of the measurements was determined by a correlation of the quantitative results from different testing systems for detection of the same analytes. The object of the correlation analysis was the proteolytic system according to the invention on the one hand, and an ELISA according to DE 10144 905 and EP1097132 on the other hand. The methods differed primarily in the sample preparation. The proteolytic method was carried out as described in Example 1. FIG. 1 and table IV shows a correlation of the measurements.

TABLE IV

Correlation of the results using a conventional ELISA and the proteolytic method

| SAMPLE | RESULT CONVENTIONAL METHOD nmol/L | RESULT PROTEOLYTIC METHOD nmol/L |
|---|---|---|
| Plasma 1 | 5 | 4.2 |
| 2 | 20 | 22.9 |
| 3 | 40 | 32.2 |
| 4 | 5 | 9.6 |
| CS | 30 | 13.6 |
| Serum1 | 50 | 63.9 |
| 2 | 10 | 10.6 |
| 3 | 20 | 27.1 |
| 4 | 30 | 23.2 |
| DS1 | 12 | 2.9 |
| DS2 | 11 | 2.3 |
| High 1 | 150 | 81.4 |
| 2 | 90 | 50.6 |
| 3 | 101 | 96.7 |

DS = deficient-serum;
High = Sera with known high 25-OH-Vit.D levels;
CS = own blood plasma The correlation analysis shows distinct advantages for the proteolytic protol of the invention and the direct measurement in serum. Especially in the case of deficient sera, too high values result after dissociations, wherein presumably vitamin D binding serum and plasma proteins, such as VDBP (Gc-globulin) bind the vitamin D tracer to the solid phase. Hence, the Gc-globulin level in the serum or plasma interferes with the vitamin D determination. The correlation analysis shows a deviating regression at low vitamin D values.

Further, the method according to the invention was compared to a commercial vitamin D enzyme immunoassay of IDS Ltd., UK. The IDS 25-hydroxyvitamin D kit is an enzyme immunoassay for the quantitative determination of 25-hydroxyvitamin D and other hydroxylated metabolites in serum or plasma. In this, standard, controls and samples are treated with an IDS-proprietory dissociation buffer (containing probably warfarin as vitamin D displacement agent), then a known amount of 25-hydroxyvitamin D is added as a binding competitor, and the so diluted samples are incubated for 2 hours in the cavities of a microtiter plate, which are coated with a specific 25-hydroxyvitamin D antibody, then aspirated and finally the cavities are washed. The binding of biotin labelled 25-hydroxyvitamin D was detected with horseradish peroxidase labelled avidin, which selectively binds to biotin. After a further washing step, the colour development was carried out as in Example 1 in a chromogenic substrate (TMB). The absorption of the interrupted reaction mixture was measured in a microtiter plate photometer, wherein the measured colour intensity was inversely proportional to the concentration of 25-hydroxyvitamin D. The IDS test kit uses a firm-owned, non-disclosed reagent for the dissociation of 25-hydroxyvitamin D and its metabolites from the binding proteins in serum or plasma.

Figure 2:
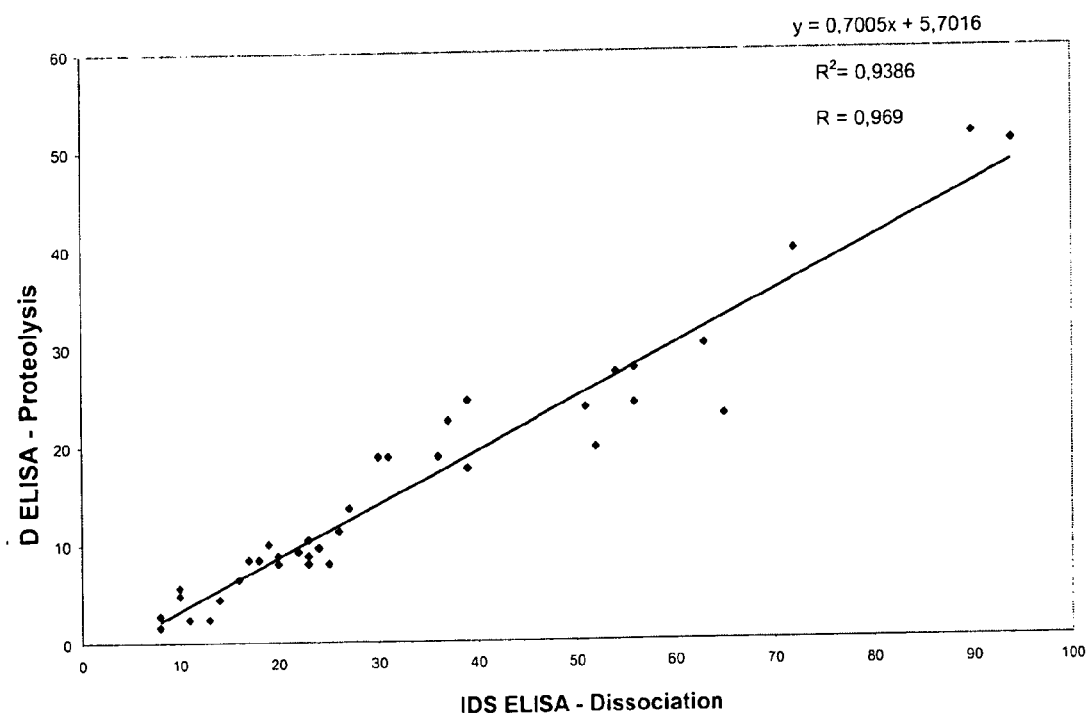
FIG. 2 shows a graphical representation of the correlation between directly measured serum 25-hydroxyvitamin D values as determined by an ELISA (1 h proteinase K digestion at 37° C.) in accordance with Example 1 of the invention and as determined by a 25-hydroxyvitamin D ELISA of Immunodiagnostic Systems Limited (IDS) Limited, UK which makes use of a IDS proprietary releasing and dissociation buffer containing warfarin.

FIG. 2 shows the correlation of the quantitative single results (84 sera) of the two methods/test for the detection of 25-hydroxyvitamin D and its hydroxylated metabolites. The results are around and parallel to the identity straight. The correlation coefficient R is 0.969. However, the regression is parallel offset. Hence, the IDS-ELISA with the dissociation method produces consistently too high values.

EXAMPLE 5

Comparison of Values Measured Using LC-MS/MS and HPLC

Figure 3:
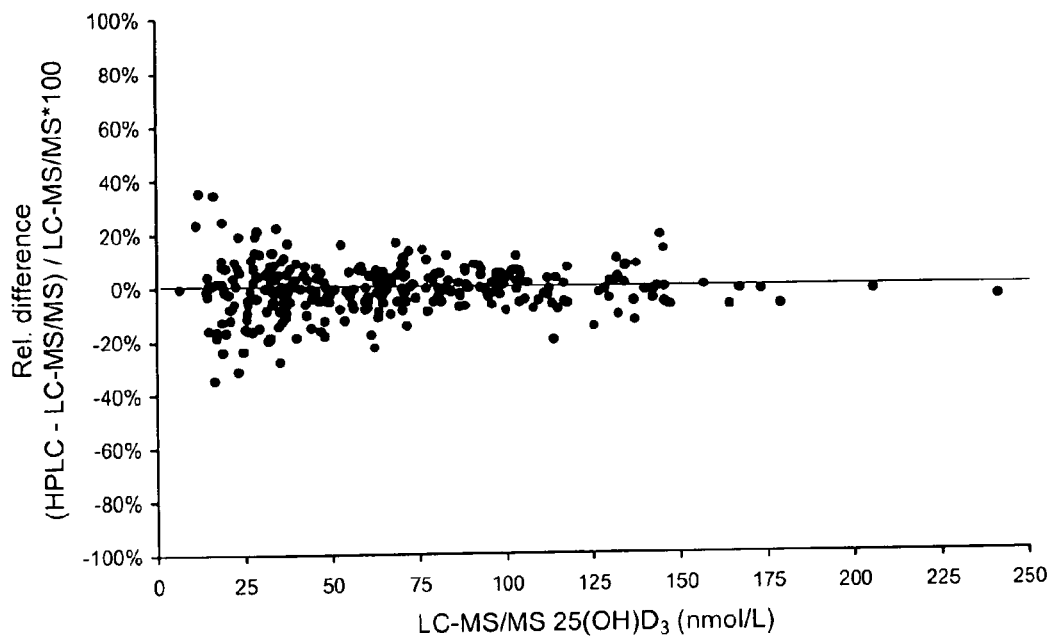
FIG. 3 shows a correlation chart of two separate established analytical reference methods for measuring vitamin D, which are LC-MS/MS and HPLC measurement.

FIG. 3 shows a correlation chart of two separate established analytical reference methods, which are measurement by HPLC and LC-MS/MS. It shows that these two methods are in good agreement so that they may be used as reference for the accuracy of the values obtained by indirect and direct vitamin D immunoassays.

Figure 4:
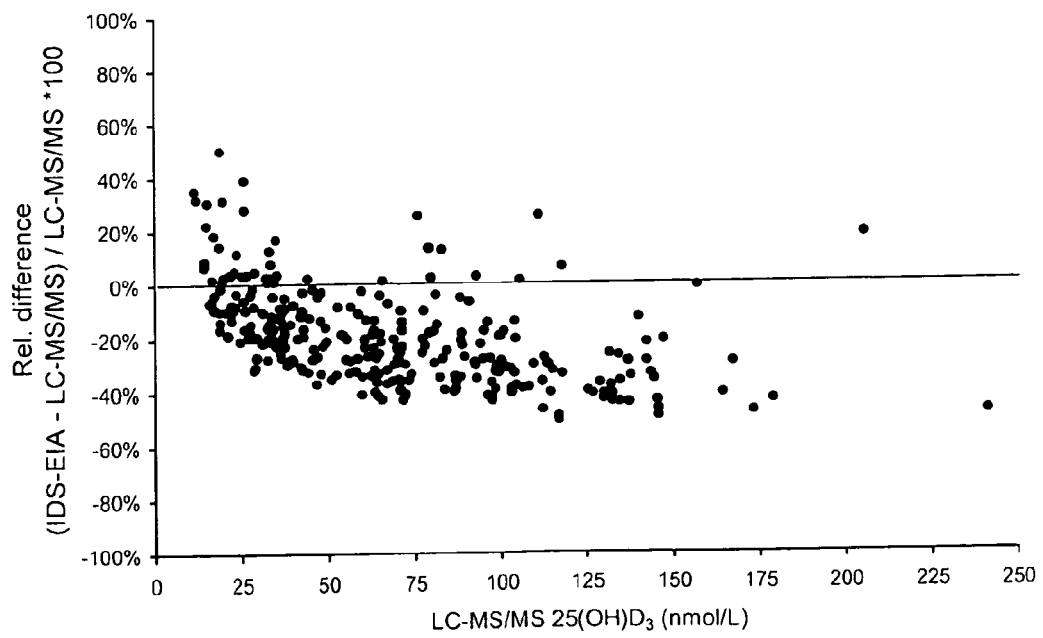
FIG. 4 shows a Bland & Altman Plot representing the relative difference between the direct serum values as obtained by the IDS-method and the reference LC-MS/MS method according to Example 5.

A set of 291 samples were analysed using the commercial IDS assay (see Example 4) and results compared with the results obtained using LC-MS/MS analysis. Sample preparation and the ELISA were carried out by strictly adhering to the instructions supplied with the test kit. FIG. 4 is a Bland & Altman Plot representing the relative difference between the measurements obtained by the two methods (Bland J M, Altman D G (1986) *Statistical method for assessing agreement between two methods of clinical measurement.* The Lancet, i, 307-310; Bland J M, Altman D G (1999) *Measuring agreement in method comparison studies.* Statistical Methods in Medical Research, 8, 135-160).

The distribution of the measurements shows that at lower (clinically relevant) concentrations, the IDS method leads to overestimated vitamin D contents, while at higher concentrations, the IDS method underestimates the vitamin D content.

A further set of 40 samples were analysed using the method according to the present invention and using HPLC measurement. The results are shown in table V.

TABLE V

Correlation of the results by proteolytic method and HPLC

| SAMPLE No. | VALUES PROTEOLYTIC METHOD µg/L | VALUES HPLC METHOD µg/L |
|---|---|---|
| 1 | 31.8 | 43.7 |
| 2 | 18.3 | 14.5 |
| 3 | 69.1 | 67.9 |
| 4 | 42.5 | 47.4 |
| 5 | 15.2 | 13.4 |
| 6 | 13.1 | |
| 7 | 59.9 | 54.8 |
| 8 | 18.5 | 12.5 |
| 9 | 53.3 | 51.1 |
| 10 | 105.5 | 113.6 |
| 11 | 23.7 | 35.0 |
| 12 | 35.0 | 33.0 |
| 13 | 29.7 | 34.7 |
| 14 | 43.4 | 32.3 |
| 15 | 87.6 | 86.2 |
| 16 | 70.3 | 59.2 |
| 17 | 63.2 | 56.7 |
| 18 | 38.8 | 39.5 |
| 19 | 26.0 | 28.8 |
| 20 | 26.3 | 27.4 |
| 21 | 29.2 | 38.7 |
| 22 | 23.8 | 23.6 |
| 23 | 48.7 | 47.0 |
| 24 | 59.1 | 54.8 |
| 25 | 27.0 | 4.5 |
| 26 | 24.7 | 23.2 |
| 27 | 70.9 | 57.0 |
| 28 | 41.9 | 41.3 |
| 29 | 50.9 | 46.0 |
| 30 | 38.3 | 61.3 |
| 31 | 25.7 | 29.2 |
| 32 | 45.3 | 39.7 |
| 33 | 39.7 | 40.6 |
| 34 | 28.1 | 23.1 |
| 35 | 44.0 | 40.5 |
| 36 | 15.4 | 17.3 |
| 37 | 98.3 | 66.9 |
| 38 | 15.8 | 16.8 |
| 39 | 46.0 | 52.7 |
| 40 | 25.5 | 23.1 |

There was no HPLC-measurement for sample 6, which is therefore disregarded. The two sets of measurements are compared using the paired samples t-test, as shown in Table VI.

TABLE VI

Paired samples t-test

| | PROTEOLYTIC METHOD | HPLC METHOD |
|---|---|---|
| Sample size | 39 | 39 |
| Arithmetic mean | 41.0000 | 42.4718 |
| 95% CI for mean | 34.0639-47.9361 | 35.1970-49.7465 |
| Variance | 457.8284 | 503.6294 |
| Standard deviation | 21.3969 | 22.4417 |
| Standard error of the mean | 3.4263 | 3.5935 |
| Mean difference | 1.4718 | |
| Standard deviation | 9.1468 | |
| 95% CI | −1.4932-4.4368 | |
| Test statistic t | 1.005 | |
| Degrees of Freedom | 38 | |
| Two-tailed probability | P = 0.3213 | |

Figure 5:
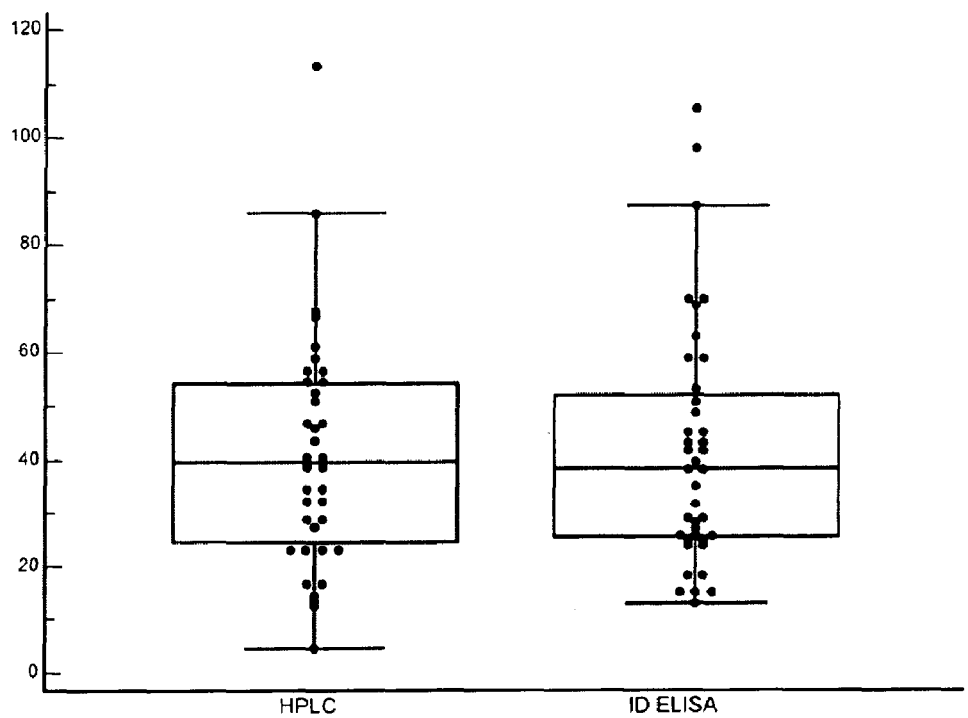
FIG. 5 shows a box and whisker plot of the measurements obtained by the method according to the invention and the reference HPLC measurements, according to Example 5.
Figure 6:
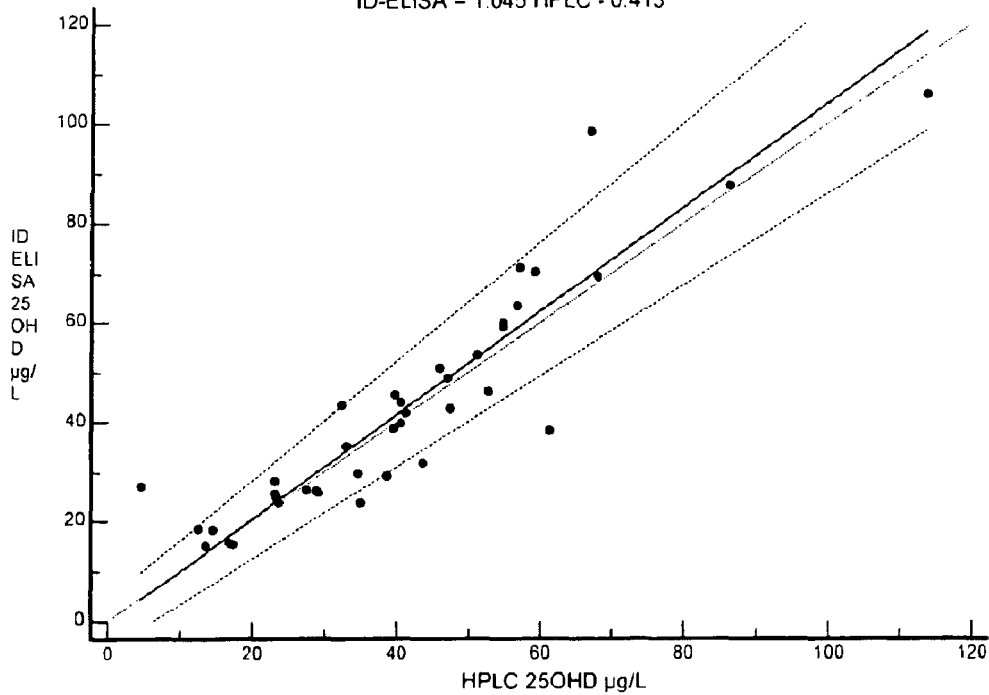
FIG. 6 shows a correlation plot of the measurements obtained by the method according to the invention and the reference HPLC measurements, according to Example 5.
Figure 7:
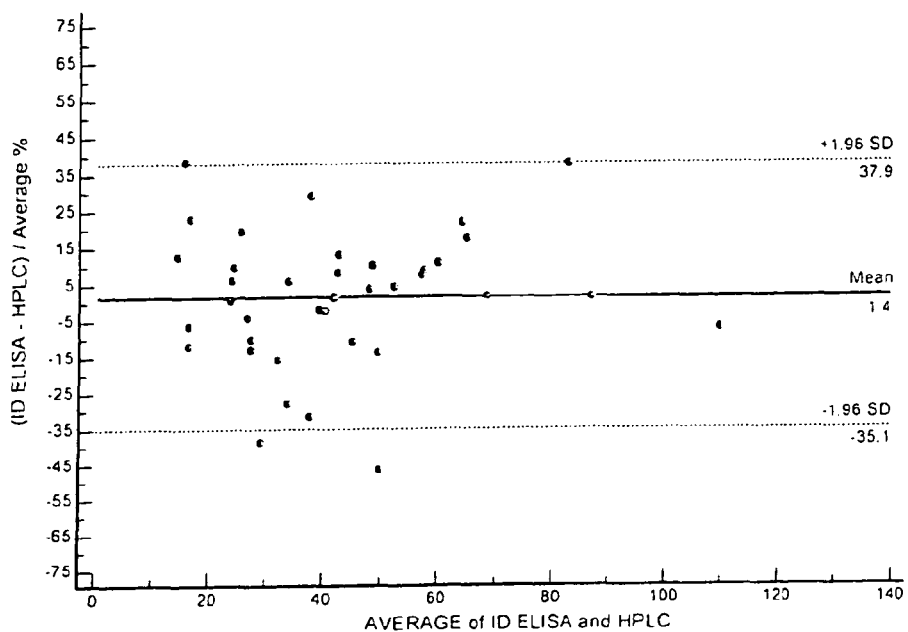
FIG. 7 shows a Bland & Altman plot representing the percentage difference between the measurements obtained by the method of the invention compared to the average measures obtained according to Example 5.

The paired samples t-test shows that there is no significant difference between the measurements obtained by the method according to the invention compared to the HPLC reference measurements. FIG. 5 is a box and whisker plot of the measurements obtained by the two methods, which shows the similar distribution pattern obtained by the measurements using the method of the invention and the reference method. FIG. 6 is a correlation plot of the two methods, which visualises the close agreement of the values obtained by the methods. FIG. 7 shows the percentage difference between the results using the method of the invention compared to the reference HPLC measurements. It shows the very low overestimation (<2%) by the proteolytic method compared to the reference, and the consistency of the measurements.

Figure 8:
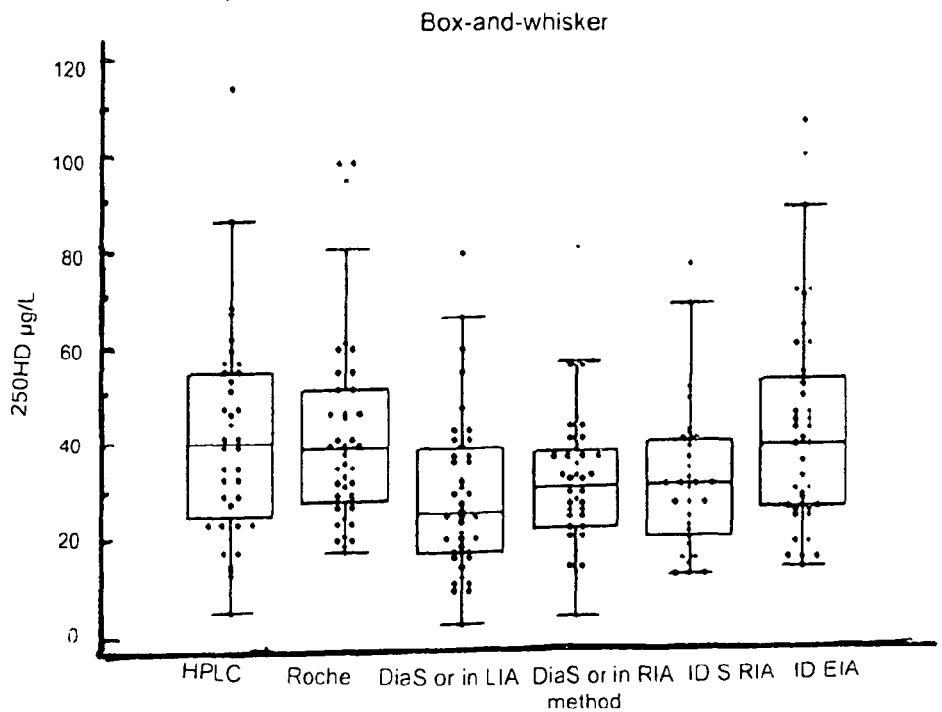
FIG. 8 shows a box-and-whisker plot comparing the vitamin D serum values obtained by the direct proteolytic method according to the invention (ID EIA), a direct dissociation method (IDS RIA) and three indirect commercial methods (Roche, DiaSorin RIA and DiaSorin LIA) and the serum values obtained by the reference HPLC.

The samples were further analysed using different commercial methods. The distribution of the results is represented in the Box-and-whisker plot FIG. 8. This shows that the DiaSorin (LIA and RIA) vitamin D assays (DiaSorin S.p.A.) and the IDS assay give consistently too low results compared to the HPLC reference measurements, while the method of the invention, as well as the Elecsys Vitamin D assay (Roche Diagnostics) test read comparable to the reference. The Roche test is an indirect method, however, and requires sample preparation which is disadvantage compared to the method of the invention.

These results clearly show that the direct measurement method according to the invention gives a better correlation with the established reference methods compared to the prior art.

The invention claimed is:

1. A method for quantitating vitamin D metabolites directly in blood plasma or serum, without the need for prior purification of the vitamin D metabolites, comprising the following steps:
   (a) adding of an effective amount of a serine protease with endo- and exoproteolytic activity to a sample containing blood plasma or serum and carrying out a digestion of the vitamin D binding proteins in the blood plasma or serum until they can no longer bind any vitamin D metabolites;
   (b) diluting of said sample containing serine protease, vitamin D metabolites and the digested plasma or serum proteins using a dilution buffer in which the serine protease is substantially inactive;
   (c) providing of a vitamin D tracer composition which is coupled to a solid phase;
   (d) providing of a monoclonal antibody against the relevant vitamin D metabolites;
   (e) combining of the sample with the vitamin D metabolites, the solid phase with the vitamin D tracer composition and the monoclonal antibody, and conducting a competition binding for a pre-determined period of time between vitamin D metabolites, vitamin D tracer bound to a solid phase and monoclonal antibody in a binding buffer in which the serine protease is substantially inactive,
   (f) separating of the solid phase with the vitamin D tracer compound and bound monoclonal antibody from the binding buffer, and optionally washing of the solid phase; and
   (g) determining of the amount of monoclonal antibody on the solid phase, and quantitating the vitamin D metabolites in the blood plasma or serum by correlation with standard samples.

2. The method of claim 1, wherein the serin protease is proteinase K.

3. The method of claim 1, wherein the monoclonal antibody binds one or more of 25-hydroxyvitamin $D_3$, 25-hydroxyvitamin $D_2$, 1α,25-dihydroxyvitamin $D_2$ and 1α, 25-dihydroxyvitamin $D_3$.

4. The method of claim 1, wherein the directly measured vitamin D metabolite is selected from the group consisting of 25-hydroxyvitamin $D_2$, 25-hydroxyvitamin $D_3$, 1α,25-dihydroxyvitamin $D_2$, 1α,25-dihydroxyvitamin $D_3$.

5. The method of claim 1, wherein the protein binding assay is one of ELISA (enzyme-linked immunosorbent assay), RIA (radioimmunoassay), FIA (fluorescence immunoassay), LIA (luminescence immunoassay), or ILMA immunoluminometric assay.

6. The method of claim 1, wherein the protein digestion of step a) is performed within a pH range of 6.0 to 10 in the presence of 0.1 to 10 mg/ml of one or more protein denaturing agents and vitamin D releasing agents selected from salicylic acid, toluene sulfonic acid, naphthalene sulfonic acids, analinonaphthalene sulfonic acids, sodium dodecylsulfate, warfarin.

7. Test kit for quantitating vitamin D metabolites directly in blood plasma or serum, comprising at least
  (i) one or more vitamin D metabolite specific antibodies,
  (ii) a vitamin D tracer which is coupled to a solid phase,
  (iii) proteinase K as a stock solution,
  (iv) a buffer for use with proteinase K comprising one or more protein denaturing agents and vitamin D releasing agents selected from salicylic acid, toluene sulfonic acid, naphthalene sulfonic acids, analinonaphthalene sulfonic acids, sodium dodecylsulfate, warfarin;
  (v) a buffer for use with the competitive binding assay further comprising an inhibitor of proteinase K.

8. The test kit of claim 7, wherein buffer (v) comprises 0.1 to 50 mM EGTA and 0.5 to 10% (w/w) of salicylic and derivatives thereof.

9. The test kit of claim 7, wherein buffer (iv) comprises denaturing agents and vitamin D releasing agents in an amount for obtaining a final concentration of 0.1 to 10 mg/mL.

10. Apparatus for quantitating vitamin D metabolites directly in blood plasma or serum, wherein the method of claim 1 is employed for fully automated analysis of serum and plasma samples.

11. Apparatus for quantitating vitamin D metabolites directly in blood plasma or serum, wherein the test kit of claim 7 is employed for fully automated analysis of serum and plasma samples.

* * * * *